United States Patent [19]
Meneghini et al.

[11] Patent Number: 5,112,739
[45] Date of Patent: May 12, 1992

[54] ENZYME CONTROLLED RELEASE SYSTEM

[75] Inventors: Frank A. Meneghini, Arlington; Paul S. Palumbo, West Newton, both of Mass.

[73] Assignee: Polaroid Corporation, Cambridge, Mass.

[21] Appl. No.: 227,141

[22] Filed: Aug. 2, 1988

[51] Int. Cl.$^5$ .............................................. C12Q 1/54
[52] U.S. Cl. ...................................... 435/14; 435/4; 435/18; 435/19; 435/21; 435/24; 435/183; 436/546
[58] Field of Search ...................... 435/18, 21, 24, 183, 435/6, 222, 4, 14, 19; 548/201, 146; 436/546; 437/7; 536/18.2, 18.7, 1.1; 544/309

[56] References Cited

U.S. PATENT DOCUMENTS

| | | |
|---|---|---|
| 3,674,478 | 7/1972 | Grasshoff et al. |
| 3,685,991 | 8/1972 | Grasshoff et al. |
| 3,698,898 | 10/1972 | Grasshoff et al. |
| 3,932,480 | 1/1976 | Grasshoff et al. |
| 4,716,222 | 12/1987 | Wallenfels et al. ................ 536/18.7 |

FOREIGN PATENT DOCUMENTS 0261931  3/1988  European Pat. Off.

OTHER PUBLICATIONS

March, Jerry; Advance Organic Chemistry; McGraw-Hill Book Company; pp. 274-277 (1968).
Hutchins et al.; Journal of the American Chemical Society; vol. 95; pp. 2282-2286; (1973).
PCT International Application No. PCT/US 86/00240 (International Publication No. WO 86/04681).
Use of o- and p-Hydroxybenzyl Functions as Blocking Groups Which Are Removable with Base, Taylor et al., J. Org. Chem., 43, pp. 1197-1200 (1978).
1,4- and 1,6-Eliminations from Hydroxy- and Amino-- Substituted Benzyl Systems: Chemical and Biochemical Applications, Wakselman, Nouveau J. de Chemie, 7, No. 7—1983, pp. 439-447.

*Primary Examiner*—Sam Rosen
*Attorney, Agent, or Firm*—Gaetano D. Maccarone

[57] ABSTRACT

This invention relates to an enzyme-controlled release method for the release of a leaving group comprising: contacting a compound represented by the formula

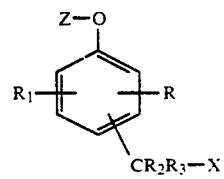

wherein R, $R_1$, $R_2$ and $R_3$ each independently is hydrogen, a substituent affecting the mobility or reactivity of the compound or a substituent including a biologically active group;
X is leaving group;
Z is an enzyme substrate moiety;
—$CR_2R_3X$ is either ortho or para to the —O—Z moiety;
with an active capable of cleaving said enzyme substrate moiety Z from said compound:
whereby said leaving group X is released from said compound.

13 Claims, No Drawings

ENZYME CONTROLLED RELEASE SYSTEM

BACKGROUND OF THE INVENTION

The present invention is concerned with systems for the controlled release of a desired moiety on demand and, more particularly, relates to such systems which utilize a quinone-methide elimination reaction mechanism for the release of such moiety.

Compounds and systems for the controlled release of a specific moiety have been the subject of considerable research and development for a variety of different applications. For example, enzymes and enzyme conjugates are well recognized reactants in immunoassays for reaction with specific substrates by which a variety of different chromophoric and fluorescent dyes are released. These enzymes and enzyme conjugates can be utilized in mobile and immobilized formats in which the rate of enzymatic reaction and/or the concentration of enzyme reaction product provides qualitative and quantitative data. Illustrative of such release systems is PCT published application WO 86/046 81 which describes a release system wherein reducible compounds release a detectable species through an intramolecular nucleophilic displacement reaction.

In addition, non-enzymatic release systems are known such as that wherein a quinone-methide elimination reaction is utilized in photographic processes to release a photographically useful group during photographic development in the presence of alkali. Such quinone-methide release systems reflect the work of Taylor et al, *J. Org. Chem.*, 43:6 (1978) pp. 1197–1200. The quinone-methide elimination reaction mechanism, as it relates to photographic processes and products, is described in U.S. Pat. Nos. 3,674,478; 3,685,991; 3,698,898 and 3,932,480.

In view of the present interest in release systems for providing a desired molecule on demand there is a continuing need for new release systems which are controlled by the action of an enzyme.

It is therefore an object of the invention to provide a novel enzyme - controlled release system.

It is another object to provide a release system wherein a desired moiety is released on demand by means of a quinone - methide elimination reactions.

A further object is to provide an enzyme - controlled immunoassay system.

Yet another object is to provide a system for the controlled release of a pharmacologically active ligand.

BRIEF SUMMARY OF THE INVENTION

These and other objects and advantages are accomplished in accordance with the invention by providing an enzyme-controlled release system by which a desired moiety may be released on demand by means of a quinone - methide elimination reaction which is initiated through the action of an active enzyme. The enzyme - controlled release system utilizes a compound represented by the formula

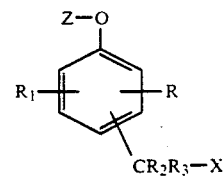

wherein $R$, $R_1$, $R_2$ and $R_3$ each independently is hydrogen, a substituent affecting the mobility or reactivity of the compound or a substituent including a biologically active group;

X is a leaving group and may be an organic moiety, an organometallic moiety or an inorganic moiety;

Z is an enzyme substrate which is cleavable by an active enzyme; and

—$CR_2R_3X$ is either ortho or para to the —O—Z moiety.

The release system may be viewed as involving a stepwise reaction sequence, it being understood that the steps may occur substantially simultaneously to release the desired moiety. The first reaction step involves the action of an active enzyme upon the enzyme substrate, Z, to cleave the substrate moiety from the compound thereby providing a reactive intermediate. The reactive intermediate then undergoes a quinone-methide elimination reaction sequence to release the leaving group, X, in anionic, neutral or cationic form.

DESCRIPTION OF THE PREFERRED EMBODIMENTS

The reaction mechanism by which the leaving group may be released on demand according to the present invention may be illustrated by the following sequence:

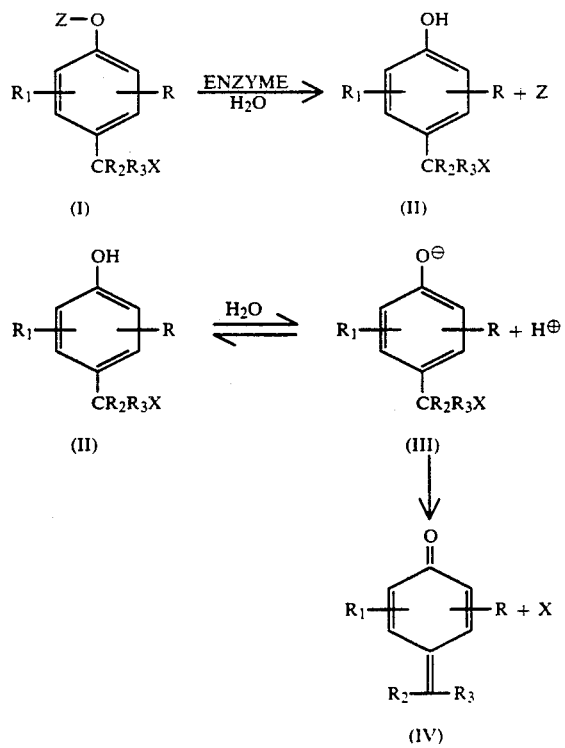

As illustrated, the active enzyme cleaves the substrate Z from the compound to form intermediate II which is in equilibrium with reactive intermediate III. The reactive intermediate in turn undergoes a quinone - methide elimination in aqueous medium to form the quinone-methide (IV) from which the leaving group X has been released. Depending upon the nature of Z and X in any instance, the rate of release of X may be dependent primarily upon the rate of enzymatic attack or the rate of release of X from reactive intermediate III.

The acidity of intermediate II is important in the quinone - methide elimination reaction and the acidity is affected by the structure of the molecule; for example, a substituent can make intermediate II more or less acidic. Generally, the reaction may proceed when the pH of the reaction medium is above the pKa of II, and the reaction becomes progressively faster as the pH becomes higher It is preferred that the pKa of II be less than the pH of the reaction medium at which the reaction sequence is desired to be conducted. It should also be noted that the rate of the step in which the active enzyme cleaves the substrate moiety, Z, from the compound is dependent to some extent upon the position of the $-CR_2R_3X$ group with respect to a particular enzyme. Accordingly, the positioning of the $-CR_2R_3X$ group, whether ortho or para to the $-O-Z$ moiety, is dependent in part upon the particular active enzyme employed and the positioning of the substituent(s) is dependent in part upon the effect on the pKa of the phenol intermediate (II). The selection of a particular substituent may also be dictated by its ability to provide a site for immobilizing the molecule to a solid support or to provide improved solubility for the molecule.

R and $R_1$ each independently can be hydrogen, a substituent which affects the mobility or solubility of the compound or a substituent which includes a biologically active group. Each can be an electron withdrawing group such as, for example, $-NO_2$, $-CN$, carboxamido, etc. or an electron donating group such as alkyl, preferably having from 1 to 6 carbon atoms, substituted alkyl, aryl such as phenyl, substituted aryl, amino, dialkylamino, trimethylsilyl, etc.

When either of R or $R_1$ is a substituent which includes a biologically active group they may be represented by $-L-B$, where L is a linking group and B is a biologically active group such as an antigen, an antibody, a DNA probe, etc. The linking group, L, may be any suitable group which joins the biologically active group to the benzene ring. Various functional groups can be used in the reactions to form the linking group such as, for example, imidoesters, aldehydes, anhydrides, isothiocyanates, diazonium salts, activated disulfides (e.g., 2-pyridyldisulfides), maleimido groups, bromoacetyl groups, etc.

$R_2$ and $R_3$ each independently is hydrogen, a substituent which affects the mobility or solubility of the compound or a substituent which includes a biologically active group. Any of the substituents mentioned above with respect to R and $R_1$ may be utilized for $R_2$ and $R_3$ also.

Typical suitable moieties which may be utilized for the leaving group X include organic groups such as dyes and pharmacologically active groups, organometallic groups such as europium chelates and inorganic groups such as $TiO_2$ and $SiO_2$. Typical suitable dye moieties include hydroxyphenoxazineones such as resorufin; hydroxycoumarins such as umbelliferone; fluoresceins and substituted fluoresceins such as fluorescein, dibromofluorescein and dichlorofluorescein; rhodols (3H-xanthene-3-ones) such as 6-amino-3H-xanthene-3-ones; and hydroxyphenyleneones such as 9-hydroxy-1-phenyleneone. Typical suitable pharmacologically active groups include therapeutic drugs, enzymes, enzyme inhibitors, anti-tumor agents and the like.

In a preferred embodiment X is a dye and the controlled release system is utilized in an immunoassay method for an analyte of interest in a biological fluid such as plasma or serum. Where X is a dye it is preferably linked to the carbon atom through a linkage formed by a heteroatom such as oxygen, sulfur or nitrogen. In such systems the dye moiety released can be a different color and/or a fluorescent species. For example, where a dye such as resorufin is linked to the carbon atom through an oxygen atom, the fluorescence of the resorufin is blocked. Thus, the initial compound is substantially non-fluorescent and a fluorescent resorufin moiety is released. In addition, the fluorescent resorufin moiety is magenta whereas the initial ether compound is yellow. Where the dye moiety is fluorescein the compound is fluorescent and releases a fluorescent dye moiety. Where X is an inorganic moiety such as $TiO_2$ or $SiO_2$ (which are bound through an oxygen atom) it is possible to convert an initially hydrophobic species to a hydrophilic one by the process of the invention.

Typical suitable enzyme substrates, Z, include glycosides such as galactosides, glucosides and mannosides; and esters such as phosphate esters and amino acid esters, e.g., leucine.

In the case of $\beta$-galactosidase (e. coli) it has been found that the rate of enzyme attack on the substrate is fastest when there is a nitro group ortho to the $-O-Z$ moiety. Optimum results for release of a dye moiety, X, have been obtained when a nitro group is ortho to the $-O-Z$ moiety and the $-CR_2R_3X$ group is para to $-O-Z$.

The compounds within Formula A may be prepared by reactions which are known in the art and these will be apparent to those skilled in the art particularly in view of the specific examples which are provided below herein. Generally, the compounds are prepared by initially subjecting a phenol, appropriately substituted as desired, for example o- nitrophenol, to a Mannich reaction. The reaction product includes isomers which are separated. The desired product is then reacted with a substrate precursor, for example tetra-O-acetyl-bromogalactose, followed by converting the dimethylamino group to a chloro group by reaction with ethyl chloroformate. The chloro group is then displaced by the substituent, X, by reaction with a suitable compound, for example, by reaction with the sodium salt of a dye. Finally, the substrate group is deacetylated such as by reaction with sodium methoxide.

As discussed previously, the release system requires that an active enzyme be utilized to react with an enzyme substrate, Z, which is a part of the initial reagent compound and to initiate a reaction sequence whereby the leaving group, X, is released from the reagent. Enzymes having the specific activity to cleave the covalent bond joining the substrate, Z, to the oxygen atom are conventionally recognized and described as hydrolases, transferases and the like. Those skilled in the art are familiar with enzyme reactions, enzyme kinetics and enzyme specificity thereby making the choice of the substrate, Z, the active enzyme and the reaction conditions in any particular instance one dictated by the desired results. Specific details and descriptions of enzymes and enzyme reactions are available in Dixon and Webb, *Enzymes*, Academic Press, 1979; and Davison, Elliott and Jones, *Data for Biochemical Research*, 3rd Edition, Clarendon Press, 1986 the texts of which are hereby expressly incorporated by reference herein. A representative, but not complete, listing of individual enzymes suitable for use with specific enzymes substrates Z which are deemed to be useful in the release system of the invention follows:

| ENZYME | SUBSTRATE (Z) |
|---|---|
| alkaline phosphatase | $PO_3^{-2}$ |
| acid phosphatase | $PO_3^{-2}$ |
| β-D-galactosidase | β-D-galactose |
| α-D-mannosidase | α-D-mannose |
| β-D-glucosidase | β-D-glucose |
| thioglucosidase | glycosyl residue |
| bovine trypsin | CBZ-glycine-arginine |
| leucineaminopeptidase | leucine |
| snake venom phosphodiesterase | adenosin-5'-phosphate |
| pancreatic ribonuclease | cytidine-3'-phosphate |

The enzyme chosen for use in the controlled release system can be provided in various formats including as: a discrete enzyme; an enzyme conjugated to a ligand of known composition or activity; a mobile molecule in either discrete or conjugated form; and an immobilized molecule in either discrete or conjugated form.

As a discrete entity the enzyme only has to demonstrate a measurable and reproducible degree of specific activity characterized by the ability to selectively cleave the covalent bond joining the substrate, Z, to the oxygen atom. In a conjugate enzyme format the enzyme is joined in a conventional manner to a ligand having specific properties. Common examples of such ligands are: one of a specific binding pair of immunological reactants, e.g., antigens and their specific antibodies; specific binding proteins such as biotin and avidin; and hormones and their target organs. Methods for conjugating ligands to enzymes without any substantial loss or modification of the specific activity of the enzyme are known in the art and are illustrated by U.S. Pat. Nos. 4,423,143 and 4,501,692. Other such useful techniques (in a homogeneous enzyme immunoassays context) are described in U.S. Pat. Nos.: 3,852,157; 4,067,774; 4,190,496; 4,191,613; 4,203,802; 4,282.352 and 4,376,825 respectively.

As regards the immobilization of either discrete or conjugated enzymes, the specific manner and chemical reactions by which the enzyme is attached to a solid phase surface or carrier may be chosen from those known in the art. Such immobilization techniques and processes by which the enzyme is attached directly or by the use of linking groups to solids such as polymeric materials, test tubes, discs, agarose and plastic beads, porous glass and polyacrylamide gels are described in *Methods In Enzymology*, Academic Press, 1980; Updike, *Antibotics and Chemotherapeutics* 26:67 (1979); and U.S. Pat. Nos. 3,739,445; 3,970,429 and 4,138,474.

As described previously the action of the active enzyme upon the substrate group, Z, results in the cleavage of the substrate group and the formation of an intermediate which undergoes a quinone - methide elimination reaction sequence in aqueous solution to cause the release of the leaving group, X. This moiety is attached to the benzene ring through a carbon atom which may itself be substituted by various substituents as has been previously described.

The initial compound, represented by Formula A, may be itself be a mobile species or it may be immobilized by being attached to a solid phase surface or carrier through any one of R, $R_1$, $R_2$ or $R_3$. Techniques and reactions by which such immobilization of the molecule can be accomplished are known in the art. Where the molecule is immobilized to a support the release system can be utilized to provide a mobile species from the initially immobile molecule. A wide variety of different alkyl and aryl groups are known for connecting the molecule to an immobile support. A particularly preferred group for this purpose is the piperazinyl sulfonyl series represented by

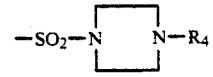

wherein $R_4$ is hydrogen or a lower alkyl radical bonded directly to a solid surface or carrier.

The selection of the leaving group, X, is a function of the intended use. The releasable moiety can take the form of a chromophoric, fluorescent or chemiluminescent dye; a dye precursor; a specific amino acid such as serine, cystein, tyrosine, lysine, glutamic acid or the like; or be a biologically active species such as, for example, therapeutic drugs, steroids, or polypeptides, which permit them to be attached to the carbon linkage without substantially affecting the biological properties of the molecule as a whole. This last category includes particularly polypeptides of recognized specific activity such as enzymes, polypeptides able to bind specifically to another molecule such as a hormone; and polypeptides having defined pharmacological properties such as tissue plasminogen activator (tPA).

As noted previously the enzyme - controlled release system and the compounds used therein in combination with an active enzyme can be used in a variety of different applications. Different features and characteristics of the invention are utilized to advantage in these modes of use. One preferred mode of use is in the field of immunoassays for chemical or diagnostic analyses. In this mode the active enzyme is covalently bonded to a ligand having known specific binding properties for an analyte of interest. Typically, an immobilized analyte analogue is employed to provide a competition between the analyte of interest and the analyte analogue for the binding sites of the ligand (the specific binding partner) joined to the enzyme. The specific binding partner, or ligand, joined to the enzyme will be a protein or a polypeptide and may functionally be classified as an antibody (monoclonal or polyclonal), an antibody fragment (such as an Fab fragment or Fab' fragment), or a specific binding molecule such as avidin or biotin. The analyte of interest demonstrates a specific binding affinity for the ligand attached to the enzyme and is typically identified as an antigen or a hapten, a specific binding protein or a molecule having specific receptor sites for the ligand. The analyte analogue typically is a chemical species identical or similar to the analyte of interest and is also chosen on the basis of its demonstrated ability to selectivity bind to the ligand previously joined to the enzyme. After the interaction of the immunological components and subsequent washing to remove any unbound species, the ligand - enzyme complex is brought into reactive contact with the molecule containing the substrate, Z, and the leaving group X so that the latter moiety is released. In this manner the presence and concentration of one or more analytes of interest can be detected with precision and accuracy.

Another mode of use is in enzyme triggered fluorescence assays. Although this mode of use is a general one it is particularly applicable to the immunoassay mode described above. The compound (Formula A) brought into reactive contact with an appropriate active enzyme or with the immunological ligand - enzyme complex described above comprises a moiety X which is a fluorescent dye. While attached to the molecule the dye moiety does not exhibit any meaningful fluorescence or exhibits a change in its excitation maxima. The attack of the enzyme or enzyme - ligand complex cleaves the substrate and in turn the fluorescent dye moiety is released as a mobile entity into the reaction medium. Upon release and the introduction of light of the appropriate wavelength, the mobile dye will fluoresce and be detectable. In this manner this mode of use can provide either a qualitative or a quantitative assay. Further, in this mode of use the molecule including the fluorescent (or chromophoric or chemiluminescent) dye may be used either as a mobile reactant or as an immobilized reactant joined to a solid carrier. The ability to immobilize the reactant molecule comprising a dye precursor and subsequently to release from it a mobile dye is an important feature of the invention.

Analytical systems which require enzyme amplification constitute another mode of use. In many instances where the detection of an enzyme is the goal of the assay a major drawback of some known detection systems is their relative insensitivity and/or inability to provide sufficient quantities of an identifying label with respect to the quantity of enzyme in the test sample. More precisely, although conventional reactants interact with the enzyme in the sample, that quantity of identifying label which is released by the test system as an indication of reactive contact is often insufficient to be measured by existing instrumentation for the analysis to be made accurately. This is especially true in assays for the detection of analytes or metabolites such as specific enzymes which are present in nanogram or picogram quantities. The present invention can provide for the amplification of such detection systems using the release system in series or multiple stages. For example, if the detection of beta-galactosidase were the goal of the assay, a first stage reactant could comprise an immobilized molecule comprising a substrate, Z, specific for beta-galactosidase and a releasable moiety, X, which is another active enzyme having a broader substrate range such as amylase. The amylase enzyme moiety would be joined to the immobilized molecule by one of its constituent lysine, tyrosine, serine, or thiol residues via its extending side groups. A second stage molecule would also be provided as a second immobilized reactant in which another substrate, Z', would be opened to attack by the displaced amylase enzyme moiety after it is released. The releasable moiety, X', of the second stage reactant would be a measurable dye, either chromophoric, fluorescent or chemiluminescent.

In the analytical protocol, the presence of $\beta$-galactosidase in the test sample would initiate an attack on the first immobile reactant and cause the release of the amylase enzyme as the first displaced X moiety; the released amylase would then be able to react with the second immobile reactant having its own substrate, Z', open to attack by the released amylase which, in turn, will cause the release of an identifiable dye as the second displaced X' moiety. The concentration of the second immobile reactant would typically be much greater than the concentration of the first immobile reactant to achieve the amplification effect. Accordingly, a single molecule of $\beta$-galactosidase (through the two-stage enzyme controlled release system) will cause the release of many molecules of identifiable dye in an amount sufficient to be reproducibly and accurately measured by conventional photometric means. In this manner, the presence of minute quantities of $\beta$-galactosidase in the test sample can be amplified using the present invention to achieve positive detection and quantitative measurement.

The release of specific agents on demand is another mode of use which is utilized when release on demand is required or desirable in response to a specific triggering event. Such situations include the release of a therapeutic drug, protein or a pharmacologically active agent; or the release of a molecule having specific properties and characteristics. In such situations the initial compound will include the agent to be released as the X moiety. The addition of the active enzyme able to cleave the substrate, Z, will cause the release of the desired agent directly on demand. In this manner the desired agent will be in the attached state subject to immediate release upon the introduction of an appropriate active enzyme.

The invention will now be described further in detail with respect to specific preferred embodiments by way of examples it being understood that these are intended to be illustrative only and the invention is not limited to the materials, processes, conditions, etc., recited therein.

EXAMPLE I

A mixture of o-nitrophenol (1.0g, 7.19 mmoles), 37% aqueous formalin solution (0.81 ml, 10.78 mmoles) and 25% aqueous dimethylamine solution (1.9 ml, 10.78 mmoles) in 25 ml absolute ethanol was refluxed overnight and the volatile components then removed on a rotary evaporator. The resulting residue was chromatographed on silica gel (silica Woelm ® 32–63 $\mu$ from Universal Scientific Inc.) using 5% methanol in methylene chloride as the eluent. The first major yellow band to elute contained 0.3g (23% yield) of 4-dimethylaminomethyl-2-nitrophenol. The next yellow band to elute contained 0.3g (23% yield) of the isomeric product, 2-dimethylaminomethyl-5-nitrophenol. The bismannich product remained on the column. The same results were obtained by using N,N,N',N'-tetramethyldiaminomethane instead of the dimethylamine and formalin.

A mixture of 4-dimethylaminomethyl-2-nitrophenol (270 mg, 1.2 mmoles), 2,3,4,6-tetra-O-acetyl-$\alpha$-D-galactopyranosyl bromide (1.0g, 2.4 mmoles), benzyltriethylammonium chloride (274 mg, 1.2 mmoles) and 0.3M sodium hydroxide (6 ml, 1.8 mmoles) was combined with 10 ml methylene chloride and stirred vigorously at room temperature under nitrogen for 7 hours. The layers were separated, the aqueous phase washed with additional methylene chloride and the combined organic phases dried over anhydrous sodium sulfate and evaporated to dryness. The resulting residue was taken up in ether and washed repeatedly with 1N sodium hydroxide until the washings were colorless. After evaporation of the solvent the residue was chromatographed on silica gel with 5% methanol in methylene chloride as the eluent (Rf on TLC 0.5) to yield 0.6g (90% yield) of (4-dimethylaminomethyl-2-nitrophenyl)2,3,4,6-tetra-O-acetyl-β-D-galactopyranoside as a colorless solid.

$^1$H NMR (CDCl$_3$) δ 2.0 (S, 3H), 2.09 (S, 3H), 2.12 (S,3H), 2.2 (S,3H), 2.22 (S,6H), 3.4 (S,2H), 4.05 (m,1H), 4.1–4.3 (m, 2H), 5.0–5.1 (m, 2H), 5.4–5.6 (m, 2H), 7.3 (d, J=7HZ, 1H), 7.45 (d, J=7HZ, 1H), 7.75 (bs, 1H).

A solution of this galactopyranoside compound (360 mg, 0.68 mmole) in 10 ml of ethylene chloride was treated with ethyl chloroformate (98 μl, 1.03 mmoles) and the resulting mixture was stirred overnight at room temperature. Another 100 μl of ethyl chloroformate and 50 mg of anhydrous sodium carbonate were added and the mixture again stirred overnight. The solution was filtered and evaporated to dryness to give 350 mg (100% yield) of (4-chloromethyl-2-nitrophenyl)-2,3,4-6-tetra-O-acetyl-β-D-galactopyranoside as an oil which slowly crystallized.

$^1$H NMR (CDCl$_3$) δ2.0 (S, 3H), 2.05 (S, 3H), 2.1 (S, 3H), 2.15 (S, 3H), 3.9–4.3 (m, 3H), 4.55 (S, 2H), 4.9–5.15 (m, 2H), 5.4–5.6 (m, 2H), 7.3 (d, J=7HZ, 1H), 7.5 (dd, J$_1$=7HZ, J$_2$=2HZ, 1H), 7.75 (d, J=2HZ, 1H).

EXAMPLE II

A solution of 2-bromomethyl-4-nitrophenol (0.5g, 2.15 mmoles), which was synthesized according to the method described by Kirkland, et al., *JACS* 86 (1964) 1448 and *ORG. SYN.* 20 (1940) 59, in 7 ml of acetonitrile was added dropwise to a stirred solution of diethylamine (0.56 ml, 5.39 mmoles) in 10 ml acetonitrile at 0°–5° C. After 1 ½ hours the mixture was warmed to room temperature, stirred for 45 minutes and the volatile components then removed on a rotary evaporator. The reside was taken up in ethyl acetate, washed twice with water, dried over anhydrous magnesium chloride and evaporated to dryness. The resulting crude product was purified by chromatography on silica gel using 5% methanol in methylene chloride as the eluent to give 0.22g (46% yield) of pure 2-diethylaminomethyl-4-nitrophenol as a yellow oil.

The product was galactosated by the procedure described in Example I to afford (2-diethylaminomethyl-4-nitrophenyl)-2,3,4,6-tetra-O-acetyl-β-D-galactopyranoside in 58% yield.

$^1$H NMR (CDCl$_3$) δ 1.05 (t, J=7HZ, 6H), 2.0–2.2 (3 singlets, 12H), 2.52 (q, 7HZ, 4H), 3.45 (AB quartet, J=15HZ, 2H), 4.15 (m, 3H), 5.0–5.2 (m, 2H) 5.4–5.6 (m, 2H), 6.95 (d, J=9HZ, 1H), 8.0 (dd, J$_1$=9HZ, J$_2$=3HZ, 1H), 8.4 (d, J=3HZ, 1H); MS (FB+555).

The corresponding chloromethyl compound was synthesized according to the procedure described in Example I to afford a quantitative yield of (2-chloromethyl-4-nitrophenyl)-2,3,4,6-tetra-O-acetyl-β-D-galactopyranoside.

$^1$H NMR (CDCl$_3$) δ 2.0–2.2 (3 singlets, 12H), 4.1–4.2 (m, 3H), 4.55 (AB quartet, (J=12HZ, 2H), 5.0–5.3 (m, 2H), 5.4–5.7 (m, 2H), 7.16 (d, J=9HZ, 1H), 8.16 (dd, J$_1$=9HZ, J$_2$=3HZ, 1H), 8.3 (d, J=3HZ, 1H).

EXAMPLE III

A solution of 5-carboxy-2-nitrophenol (1.0g, 5.5 mmoles), thionyl chloride (1.5 ml, 20.75 mmoles) and dimethylformamide (3 drops) in 10 ml toluene was heated to 70° and stirred for 30 minutes. The mixture was then cooled and decanted from a small amount of dark oil which had deposited on the walls of the flask. Solvent was removed under vacuum and the residue evaporated again from fresh toluene. The resulting residue was taken up in 10 ml of methylene chloride and added dropwise to a cold stirred solution of morpholine (4.8 ml, 55.0 mmoles) in 20 ml of methylene chloride. When addition was complete the mixture was stirred at room temperature for 2 hours, washed with 1N HCl, dried over anhydrous sodium sulfate and the volatile components removed under vacuum. Recrystallization of the crude product from a methylene chloride - hexane solution gave 700 mg (50% yield) of 5-morpholinamido-2-nitrophenol as pale yellow crystals.

$^1$H NMR (CDCl$_3$) δ 3.2–4.0 (m, 8H), 6.9 (dd, J$_1$=9HZ, J$_2$=2HZ, 1H) 7.05 (d, J=2HZ, 1H), 8.05 (d, J=9HZ, 1H), 10.5 (bs, 1H).

A dimethylaminomethyl group was attached in the 4-position by the procedure described in Example I to obtain a 24% yield of 4-dimethylaminomethyl-5-morpholinamido-2-nitrophenol.

$^1$H NMR (CDCl$_3$) δ 2.2 (S, 6H), 2.8–3.3 (m, 3H), 3.4–3.9 (m, 7H), 6.94 (S, 1H), 8.0 (S, 1H); MS (FB+310).

The previous product was galactosated by initially forming a solution of the compound (56 mg, 0.18 mmole), 2,3,4,6-tetra-O-acetyl-α-D-galactopyranosyl bromide (74 mg, 0.18 mmole) and silver carbonate (55 mg, 0.2 mmole) in 5 ml dry acetonitrile and stirring at room temperature under nitrogen overnight. The mixture was filtered under suction, evaporated to dryness and the residue chromatographed on silica gel using 5% methanol in methylene chloride as the eluent to give 84 mg (73% yield) of (4-dimethylaminomethyl-5-morpholinamido-2-nitrophenyl)-2,3,4,6-tetra-O-acetyl-β-D-galactopyranoside as a colorless solid foam.

$^1$H NMR (CDCl$_3$) δ 2.0 (S, 3H), 2.05 (S, 3H), 2.12 (S, 3H), 2.16 (S, 3H), 2.2 (S,6H), 2.9–3.3 (m, 3H), 3.4–4.3 (m, 10H), 4.9–5.6 (m, 4H), 7.15 (S, 1H), 7.7 (S, 1H); MS (FB+ 640).

The corresponding chloromethyl compound was synthesized according to the procedure described in Example I to give (4-chloromethyl-5-morpholinoamido-2-nitrophenyl)-2,3,4,6-tetra-O-β-D-galactopyranoside.

$^1$H NMR (CDCl$_3$) δ 1.94 (s, 3H), 2.0 (s, 3H), 0 2.06 (s, 3H), 2.14 (s, 3H), 3.1–3.3 (m, 3H), 3.5–4.2 (m, 10H), 4.8–5.1 (m, 2H), 5.3–5.5 (m, 2H), 7.15 (bs, 1H), 7.8 (s, 1H); MS (FB+ 631).

EXAMPLE IV 3-morpholinamido-2-nitrophenol was prepared by the procedure described in Example I to afford a 79% yield after recrystallization from methylene chloride-hexane.

$^1$H NMR (CDCl$_3$) δ 3.14–3.35 (m, 2H), 3.6–4.1 (m, 6H), 6.75 (dd, J$_1$=7HZ, J$_2$=2HZ, 1H), 7.1 (dd, J$_1$=7HZ, J$_2$=2HZ, 1H), 7.5 (t, J=7HZ, 1H), 10.5 (S, 1H).

Two isomers, namely (3- and 5- morpholinamido-2-nitrophenyl)-2,3,4,6-tetra-O-acetyl-β-D-galactopyranoside, respectively, were synthesized from 3-morpholinamido-2-nitrophenol and 5-morpholinamido-2-nitrophenol, respectively, according to the silver carbonate method described in Example III. The $^1$H NMR data were consistent with the structure of the compounds.

EXAMPLE V

A compound (A), namely (4-resorufinylmethyl-2-nitrophenyl)-2,3,4,6-tetra-O-acetyl-β-D-galactopyranoside (Formula A - R is O-nitro; R$_1$, R$_2$ and R$_3$ are H; —CR$_2$R$_3$X is para; X is

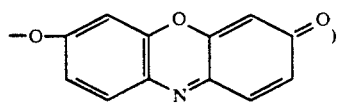

was prepared by first heating a solution of (4-chloromethyl-2-nitrophenyl)-2,3,4,6-tetra-O-acetyl-β-D-galactopyranoside (220 mg, 0.425 mmole), sodium resorufin (100 mg, 0.425 mmole) and a catalytic amount of sodium iodide in 4 ml of dry DMF at 70° C. for 4 hours. The mixture was cooled to room temperature, evaporated to dryness under high vacuum and the resulting residue chromatographed on silica gel with 5% methanol in methylene chloride as the eluent. Isolation of the high Rf orange-yellow band affords 277 mg (94% yield) of the desired product as an orange solid foam.

$^1$H NMR (CDCl$_3$) δ 2.0 (S, 3H), 2.05 (S, 3H), 2.1 (S, 3H), 2.16 (S, 3H), 4.0–4.3 (m, 3H), 5.0–5.2 (m, 2H), 5.35–5.7 (m, 2H), 6.2 (d, 2HZ, 1H), 6.65–7.1 (m, 3H); 7.3–8.0 (m, 5H); M.S. (FB+ 694).

The galactosyl acetate protecting groups were removed in the following manner: the compound (277 mg, 0.4 mmole) in 30 ml methanol was treated with 0.2 N sodium methoxide (140 μl, 0.028 mmole) and the mixture stirred overnight at room temperature under nitrogen. The product was removed by suction filtration, washed with excess methanol and dried under vacuum to provide 167 mg (79% yield) of 4-resorufinyl-methyl-2-nitrophenyl)-β-D-galactopyranoside as an orange powder.

$^1$H NMR (d$_6$DMSO + 1 drop D$_2$O) δ 3.4–3.8 (m, 6H), 5.08 (d, J=9HZ, 1H), 5.28 (s, 2H), 6.25 (d, J=2HZ, 1H), 6.78 (dd, J$_1$=9HZ, J$_2$=2HZ, 1H), 7.1 (dd, J$_1$=9HZ, J$_2$=2HZ, 1H), 7.19 (d, J=2HZ, 1H), 7.45 (d, J=9HZ, 1H), 7.5 (d, J=9HZ, 1H), 7.7–7.8 (m, 2H), 8.0 (d, J=2HZ, 1H); MS (FB+ 527).

The procedure described above is a general deprotection procedure. In cases where the product does not conveniently precipitate out, an alternate procedure can be followed wherein the solution is treated with an ion exchange resin such as Amberlite ® 410 (activated with 1N sodium acetate solution for 1 hour and then washed copiously with distilled water and finally with absolute methanol) for several minutes and then passed down a small column of the resin using methanol as the elution solvent. The eluted product is then isolated by evaporation of the solvent. This treatment effects a quantitative removal of the residual sodium methoxide and dye.

Another method for removal of the acetate groups involves treatment with 50 equivalents of triethylamine in methanol at room temperature.

EXAMPLE VI

A compound (B), according to the invention was prepared—Formula A, Z is a β-D-galactopyranoside residue; R is o-nitro; R$_1$, R$_2$ and R$_3$ are hydrogen; CR$_2$R$_3$X is para and X is

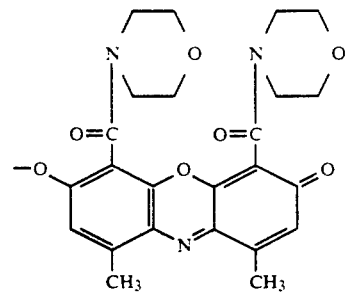

pH7 max 460 nm (ε = 21,500).

$^1$H NMR (CD$_3$OD) δ 2.5 (S, 3H), 2.75 (S, 3H), 3.4–4.0 (m, 22H), 5.1 (d, J=9HZ, 1H), 5.35 (AB quartet, J=12 HZ, 2H), 6.94 (S, 1H), 7.3 (S, 1H), 7.54 (d, J=9HZ, 1H), 7.7 (d, J=9HZ, 1H), 7.94 (S, 1H).

EXAMPLE VII

A compound (C) according to the invention was prepared—Formula A, Z is a β-D-galoctopyranoside residue; R is p-nitro; R$_1$, R$_2$ and R$_3$ are hydrogen; CR$_2$R$_3$X is ortho; and X is

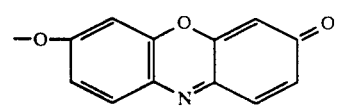

$^1$H NMR (DMSO-d6, δ 3.2–3.8 (m, 6H), 5.05 (d, J=7HZ, 1H), 5.4 (S, 2H), 6.3 (S, 1H), 6.8 (dd, J$_1$=9HZ, J$_2$=2HZ, 1H), 7.21 (dd, J$_1$=9HZ, J$_2$=2HZ, 1H), 7.3 (d, J=2HZ, 1H), 7.4 (d, J=9HZ, 1H), 7.57 (d, J=9HZ, 1H), 7.84 (d, J=9HZ, 1H), 8.3 (dd, J$_1$=9HZ, J$_2$=2HZ, 1H), 8.35 (d, J=2HZ, 1H); MS (FB+ 527).

EXAMPLE VIII

A compound (D) according to the invention was prepared—Formula A, Z is a β-D-galactopyranoside residue; R is o-nitro; R$_1$ is 5-morpholinamido; CR$_2$R$_3$X is para; and X is resorufinyl.

$^1$H NMR (d$_7$DMF) δ 3.3–4.0 (m, 14H), 5.3 (d, J=8HZ, 1H), 5.25–5.45 (m, 2H), 6.25 (S, 1H), 6.8 (d, J=7HZ, 1H), 7.2 (dd, J$_1$=7HZ, J$_2$=2HZ, 1H), 7.3 (d, J=2HZ, 1H), 7.55 (d, J=7HZ, 1H), 7.65 (s, 1H), 7.84 (d, J=7HZ, 1H), 8.25 (s, 1H); MS (FB+ 640).

EXAMPLE IX

A compound (E) according to the invention was prepared—Formula A wherein Z is a β-D-galactopyranoside residue; R is o-nitro; R$_1$, R$_2$ and R$_3$ are hydrogen; CR$_2$R$_3$X is para; and X is a dye residue represented by the formula

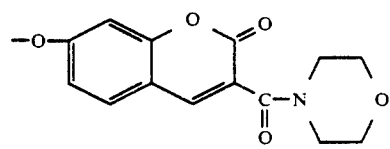

$^1$H NMR (d$_6$DMSO + 1 drop D$_2$O) δ 3.3–3.7 (m, 14H), 5.08 (d, J=8HZ, 1H), 7.1 (dd, J$_1$=7HZ, J$_2$=3HZ, 1H), 7.15 (d, J=3HZ, 1H), 7.5 (dd, J$_1$=7HZ, $J_2=3HZ$, 1H), 7.7-7.8 (m, 2H), 8.0 (S, 1H), 8.15 (S, 1H); MS (FB+ 589).

EXAMPLE X

The approximate relative release rates of the leaving groups of compounds according to the invention compared with that of o-nitrophenolgalactoside (ONPG) were measured according to the following procedure: a $5 \times 10^{-5}$ M solution of the compound was formed in pH7 tris(hydroxymethyl) aminomethane buffer which was 0.01 M in sodium chloride and 0.01 M in magnesium chloride at 25° C. The solution was placed in a 3 ml cuvette and 1.5 IU of β-galactosidase from e. coli introduced. The reaction mixture was monitored in a spectrophotometer at the appropriate wavelength. The results are shown below.

| COMPOUND | APPROXIMATE RELATIVE RATE |
|---|---|
| ONPG | 1.0 |
| A | 0.25 |
| B | 0.3 |
| C | 0.005-0.05 |
| D | 0.02 |
| E | 0.1-0.5 |

It can be seen that compounds A and C, which are isomers, have significantly different release rates. These data illustrate the preferred positions of the nitro group and the substituent including the dye moiety with respect to the particular enzyme used. In addition, compound D, which is identical to compound A except that the former also includes a morpholinamido group in the 5- position, exhibits a much slower release rate thereby indicating the effect of the substituent on the release rate where that particular enzyme was used to initiate the release mechanism.

EXAMPLE XI

A 0.3 mmolar mixture of compound B in a pH 7.0 buffer (0.1 molar $NaH_2PO$ 0.15 molar NaCl, 0.1% Zwittergent 3-14) was stirred at room temperature for 30 minutes and then filtered through a 0.22 μ filter element. The concentration of the compound was calculated by diluting the solution (1:10) to provide an optical density of between 0.39 and 0.41 at 470 nm ($\epsilon=20,000$).

The solution (100 μl) was added to a microtiter plate well and the optical density was measured at 570 nm with an EIA Auto Reader, Model EL 310 from Bio Tek Instruments. The fluorescence of the same 100 μl volume of the solution was measured with a Titertek Fluoroska ® from Flow Laboratories by exciting at 550 nm and reading at 580 nm.

To each of the 100 μl volumes of the solution there were added 10 μl of an anti α-TSH-β-galactosidase conjugate (1.3 × 10^31 11 molar in β-galactosidase) and the mixtures were incubated for 15 minutes at 37° C. followed by measuring the optical density and fluorescence as described above. These data showed a change in optical density of 0.0594 and a change in fluorescence of 7266 mV. These data illustrate that a detectable result was obtained according to the release system of the invention with an enzyme molar concentration of $1.3 \times 10^{-12}$.

EXAMPLE XII

A 0.614 mmolar solution of compound B in a pH 7.6 buffer made up of 0.01 molar $NaH_2PO_4$, 0.1 molar NaCl. 0.1 molar $NaN_3$, 2 mmolar $MgCl_2$, 0.1% Tween 20 ®, a surfactant, and 0.1% bovine serum albumin was prepared. β-galactosidase (e. coli) solutions of varying concentrations were prepared in pH 7.6 buffer made up as described above except that it did not include any BSA.

The compound B solution (45 μl was added to each of the enzyme solutions (5 μl) in a reaction chamber and the latter inserted into a laboratory instrument. The fluorescence of each reaction mixture was read initially and at 2 minutes by exciting at 550 nm and measuring the emissions at 580 nm. The table shows the change in voltage/minute (average of two separate determinations) as a function of enzyme concentration.

| Enzyme Conc. | V/min |
|---|---|
| $1 \times 10^{-13}$ | 0.035 |
| $3 \times 10^{-13}$ | 0.078 |
| $1 \times 10^{-12}$ | 0.247 |
| $3 \times 10^{-12}$ | 0.734 |
| $1 \times 10^{-11}$ | 2.161 |

These data illustrate that a satisfactory standard curve for an enzyme controlled assay according to the invention was generated.

Although the invention has been described with respect to specific preferred embodiments it is not intended to be limited thereto but rather those skilled in the art will recognize that variations and modifications may be made which are within the spirit of the invention or the scope of the appended claims. For example, the compounds within Formula A include substituents R and $R_1$. It will be understood that the cyclic ring maybe further substituted with another substituent which affects the mobility or reactivity of the compound. Thus, analogs possessing the advantageous features of the compounds used according to the invention will be considered as equivalents thereof for the purposes of the claims herein.

What is claimed is:

1. An enzyme-controlled release method for the release of a leaving group, said method comprising:
   contacting a compound represented by the formula

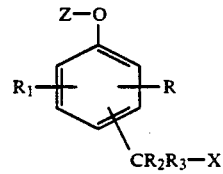

wherein R and $R_1$ each independently is hydrogen, a substituent affecting the mobility or reactivity of the compound or a substituent including a biologically active group;
   $R_2$ and $R_3$ each is hydrogen;
   X is leaving group;
   Z is an enzyme substrate moiety;
   —$CR_2R_3X$ is either ortho or para to the —O—Z moiety;
   with an active enzyme capable of cleaving said enzyme substrate moiety Z from said compound;

whereby said leaving group X is released from said compound.

2. The method as defined in claim 1 wherein said leaving group X is selected from the group consisting of an organic moiety, an organometallic moiety and an inorganic moiety.

3. The method as defined in claim 2 wherein said leaving group X is an organic dye moiety.

4. The method as defined in claim 3 wherein said organic dye moiety is fluorescent.

5. The method as defined in claim 1 wherein said leaving group X is a pharmacologically active group.

6. The method as defined in claim 1 wherein said enzyme substrate moiety Z is a glycoside, a phosphate ester or an amino acid ester.

7. A method for determining the presence of an analyte in a fluid comprising:
    contacting a fluid sample including an analyte with a binding partner of said analyte conjugated to an enzyme and an immobilized analogue of said analyte to form bound and free immunocomplexes;
    contacting said bound and free immunocomplexes with a compound represented by the formula

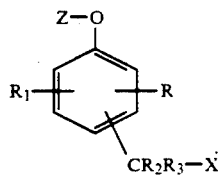

wherein R and $R_1$ each independently is hydrogen, a substituent affecting the mobility or reactivity of the compound or a substituent including a biologically active group;
$R_2$ and $R_3$ each is hydrogen;
X is leaving group;
Z is an enzyme substrate moiety;
—$CR_2R_3$X is either ortho or para to the —O—Z moiety;
wherein said active enzyme is capable of cleaving said enzyme substrate moiety Z from said compound whereby said leaving group X is released from said compound;
separating said bound and free immunocomplexes to form a solid phase and a liquid phase;
and detecting the presence of said analyte in said solid phase or said liquid phase as a function of said leaving group.

8. The method as defined in claim 7 wherein said leaving group X is an organic dye moiety.

9. The method as defined in claim 8 wherein said organic dye moiety is fluorescent and said analyte is detected in said solid phase.

10. The method as defined in claim 9 wherein said organic dye moiety is selected from the group consisting of hydroxyphenoxazineones, hydroxycoumarins, fluoresceins, rhodols and hydroxyphenyleneones.

11. The method as defined in claim 10 wherein said organic dye moiety is resorufin, umbelliferone or fluorescein.

12. The method as defined in claim 9 wherein said enzyme substrate moiety Z is a glycoside, a phosphate ester or an amino acid ester.

13. The method as defined in claim 12 wherein said enzyme is β-galactosidase, Z is a galactoside, R is a nitro group and is ortho to the —O—Z moiety and —$CR_2R_3$X is para to the —O—Z moiety.

* * * * *